(12) United States Patent
Shedrinsky

(10) Patent No.: US 8,549,600 B2
(45) Date of Patent: Oct. 1, 2013

(54) SYSTEMS, METHODS AND ANALYZERS FOR ESTABLISHING A SECURE WIRELESS NETWORK IN POINT OF CARE TESTING

(75) Inventor: Felix Shedrinsky, East Windsor, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 85 days.

(21) Appl. No.: 13/220,971

(22) Filed: Aug. 30, 2011

(65) Prior Publication Data
US 2012/0233679 A1    Sep. 13, 2012

Related U.S. Application Data

(63) Continuation-in-part of application No. 13/046,515, filed on Mar. 11, 2011.

(51) Int. Cl.
| H04L 29/06 | (2006.01) |
| H04L 9/32 | (2006.01) |
| G06F 7/04 | (2006.01) |
| G06F 15/16 | (2006.01) |
| G06F 17/30 | (2006.01) |

(52) U.S. Cl.
USPC .............................. 726/7; 713/168; 709/225

(58) Field of Classification Search
None
See application file for complete search history.

(56) References Cited

U.S. PATENT DOCUMENTS

| 4,933,048 A | 6/1990 | Lauks |
| 4,954,087 A | 9/1990 | Lauks et al. |
| 5,096,669 A | 3/1992 | Lauks et al. |
| 5,112,455 A | 5/1992 | Cozzette et al. |
| 5,124,661 A | 6/1992 | Zelin et al. |
| 5,200,051 A | 4/1993 | Cozzette et al. |
| 5,447,440 A | 9/1995 | Davis et al. |
| 5,487,069 A | 1/1996 | O'Sullivan et al. |
| 6,379,883 B2 | 4/2002 | Davis et al. |
| 6,438,498 B1 | 8/2002 | Opalsky et al. |
| 6,602,469 B1 | 8/2003 | Maus et al. |
| 6,781,522 B2 | 8/2004 | Sleva et al. |
| 6,845,327 B2 | 1/2005 | Lauks |
| 7,027,872 B2 | 4/2006 | Thompson |
| 7,041,468 B2 | 5/2006 | Drucker et al. |
| 7,235,213 B2 | 6/2007 | Mpock et al. |
| 7,263,501 B2 | 8/2007 | Tirinato et al. |
| 2002/0059030 A1* | 5/2002 | Otworth et al. .................. 702/19 |
| 2002/0156650 A1 | 10/2002 | Klein et al. |
| 2003/0093298 A1* | 5/2003 | Hernandez et al. ............... 705/2 |

(Continued)

FOREIGN PATENT DOCUMENTS

WO    WO 2009/153710 A2    12/2009

OTHER PUBLICATIONS

International Search Report and Written Opinion mailed Jul. 5, 2012 in corresponding International Application No. PCT/US2012/026898.

(Continued)

*Primary Examiner* — Shin-Hon Chen

(57) ABSTRACT

A system and method for initiating and maintaining a secure wireless communication between a wireless analyzer and a target network (e.g., a hospital network connected to a LIS and/or HIS). The present disclosure provides novel processes and systems for securely networking a wireless analyzer with a Wi-Fi network without the need for an operator or user to engage in manual initiation steps on, or through, the wireless analyzer.

39 Claims, 8 Drawing Sheets

(56) References Cited

U.S. PATENT DOCUMENTS

| | | |
|---|---|---|
| 2004/0167465 A1 | 8/2004 | Mihai et al. |
| 2004/0266449 A1* | 12/2004 | Smetters et al. ........... 455/452.1 |
| 2005/0216199 A1 | 9/2005 | Banet |
| 2006/0129432 A1* | 6/2006 | Choi et al. ........................ 705/3 |
| 2006/0278242 A1 | 12/2006 | McGlennen et al. |
| 2006/0282885 A1 | 12/2006 | Combs et al. |
| 2007/0118188 A1 | 5/2007 | von Arx et al. |
| 2007/0233395 A1 | 10/2007 | Neel et al. |
| 2007/0254614 A1 | 11/2007 | Muralidharan et al. |
| 2007/0258395 A1 | 11/2007 | Jollota et al. |
| 2007/0299316 A1 | 12/2007 | Haslehurst et al. |
| 2008/0037444 A1* | 2/2008 | Chhabra ....................... 370/254 |
| 2008/0091470 A1 | 4/2008 | Muradia |
| 2008/0097551 A1 | 4/2008 | Dicks et al. |
| 2008/0217407 A1 | 9/2008 | Ackermann et al. |
| 2009/0097793 A1 | 4/2009 | Hofmann et al. |
| 2009/0300171 A1 | 12/2009 | Bhame et al. |
| 2009/0318998 A1 | 12/2009 | Diebold et al. |
| 2009/0326981 A1* | 12/2009 | Karkanias et al. ................ 705/3 |
| 2009/0326984 A1* | 12/2009 | Ferguson ........................... 705/3 |
| 2010/0146300 A1 | 6/2010 | Brown |
| 2010/0228977 A1 | 9/2010 | Sievert et al. |
| 2011/0047603 A1* | 2/2011 | Gordon et al. .................... 726/5 |
| 2011/0245089 A1* | 10/2011 | Scott et al. ........................ 506/7 |
| 2012/0065993 A1* | 3/2012 | Arimitsu ........................... 705/2 |

OTHER PUBLICATIONS

"Wi-Fi Protected Setup Specification Version 1.0h", Dec. 31, 2006, pp. 1-110, XP 055031152.

International Search Report and Written Opinion mailed Jul. 5, 2012 in corresponding International Application No. PCT/US2012/026892.

"DirectAccess, Network Access Protection (NAP), and Certificate Server (PKI) Consulting", Agile IT. Accessed Feb. 5, 2011. http://www.agileit.com/Consulting/Windows-Platform/Pages/DirectAccess-Network-Access-Protection-NAP-Certicate-Server-PKI-Consulting.aspx.

"Securing Your Future with Two-Factor Authentication", RSA. Accessed Mar. 18, 2011. http://www.rsa.com/node.aspx?id=1156.

* cited by examiner

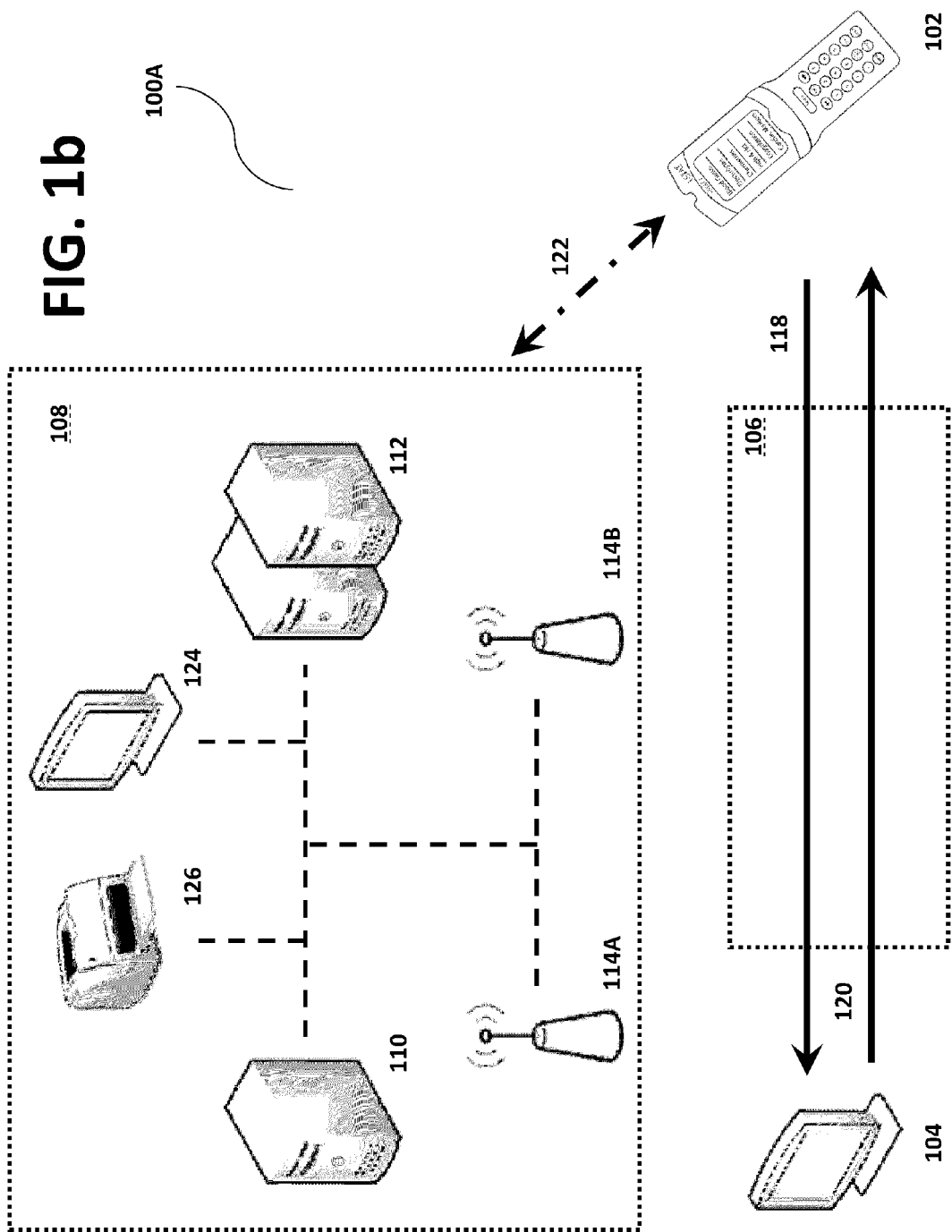

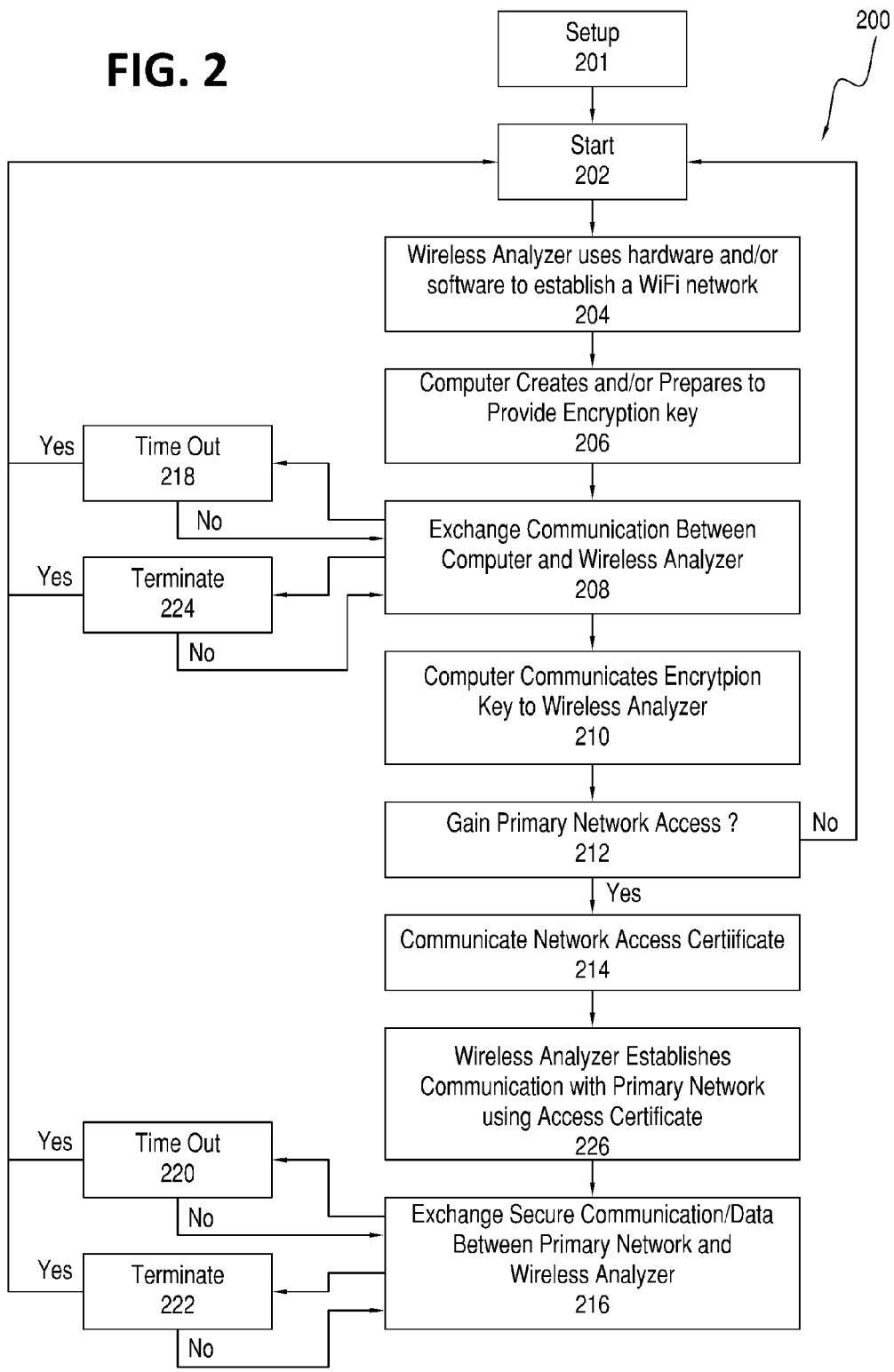

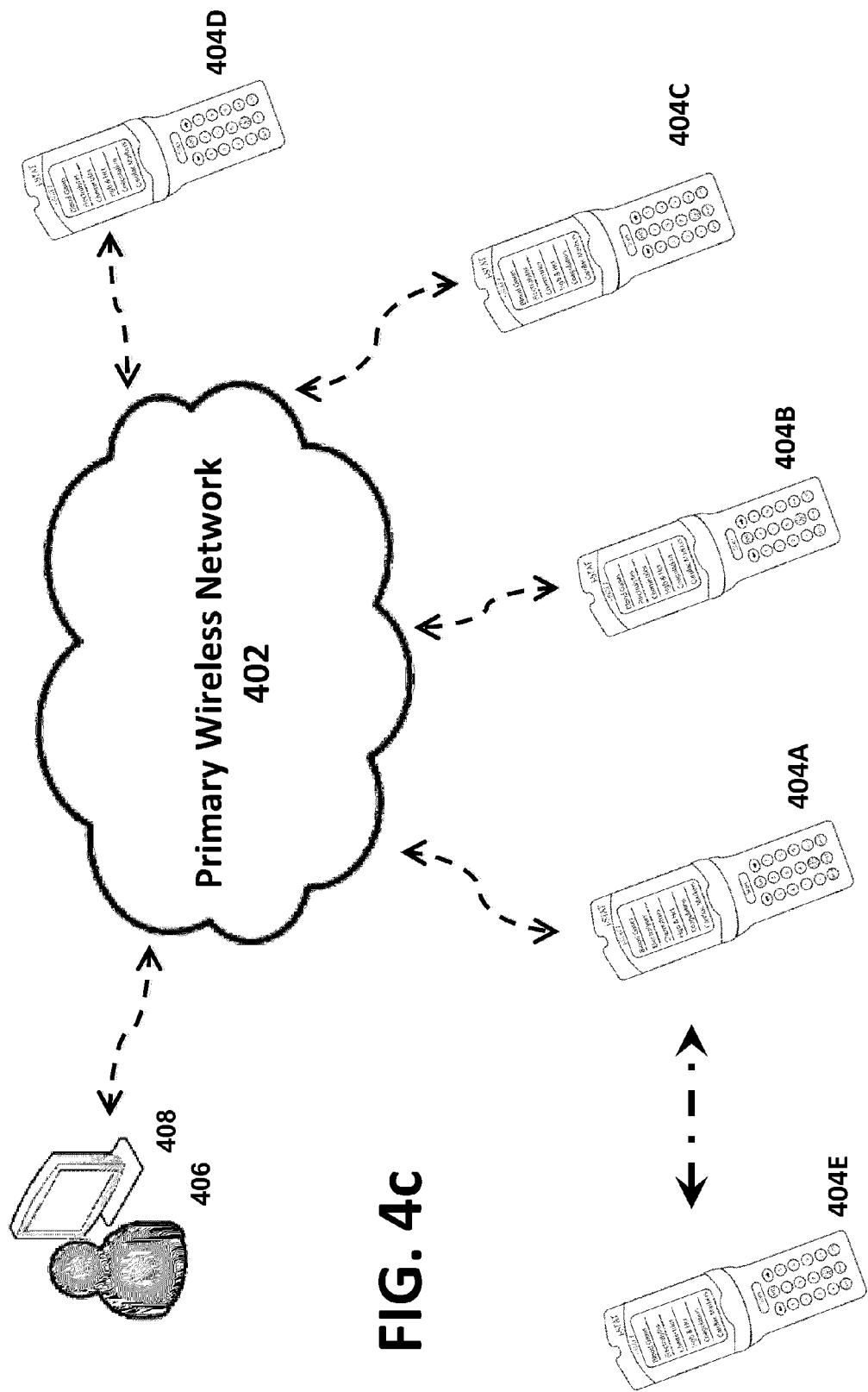

SYSTEMS, METHODS AND ANALYZERS FOR ESTABLISHING A SECURE WIRELESS NETWORK IN POINT OF CARE TESTING

CROSS-REFERENCE TO RELATED APPLICATIONS

The present application is a continuation in part of U.S. application Ser. No. 13/046,515, filed on Mar. 11, 2011, the disclosure of which is expressly incorporated by reference herein in its entirety.

FIELD OF THE INVENTION

The present invention relates to wireless medical devices and medical device networks. Specifically, the present invention relates to systems and methods for securing wireless data communication protocols and wireless data communication features for use in a medical device network environment.

BACKGROUND OF THE INVENTION

For hospitals, the recent introduction of point-of-care (POC) testing capabilities has created unique requirements for secure data transmission from point-of-care test instruments to the central data station (CDS), laboratory information system (LIS), and/or hospital information system (HIS) inventory control.

Point-of-care sample analysis systems are generally based on a reusable reading apparatus that performs sample tests using a disposable device (e.g., a cartridge or strip) that contains analytical elements (e.g., electrodes or optics for sensing analytes such as, for example, pH, oxygen, or glucose). The disposable device can optionally include fluidic elements (e.g., conduits for receiving and delivering the sample to the electrodes or optics), calibrant elements (e.g., fluids for standardizing the electrodes with a known concentration of the analyte), and dyes with known extinction coefficients for standardizing optics. The reading apparatus or instrument contains electrical circuitry and other components for operating the electrodes or optics, making measurements, and doing computations. The reading apparatus can typically display results and communicate those results to a CDS, LIS, and/or an HIS by way of a computer workstation. Communication between a reading apparatus (e.g., a point-of-care device) and a workstation, and/or between a workstation and a CDS/LIS/HIS, may, for example, be by way of an infrared link, a wired connection, a wireless communication, or any other form of data communication capable of transmitting and receiving information, or any combination thereof.

Point-of-care sample testing systems eliminate the time-consuming need to send a sample to a central laboratory for testing. Point-of-care sample testing systems allow a user e.g. a nurse and physician, at the bedside of a patient, to obtain a reliable, quantitative, analytical results, comparable in quality to that which would be obtained in a laboratory. In operation, the user may select a device with the required panel of tests (e.g., electrolytes, metabolites, cardiac markers and the like), draw a sample, dispense it into the device, optionally seal the device, and insert the device into the reading apparatus to communicate the data to an LIS/HIS for analysis. An example of such a system is the i-STAT® system sold by Abbott Point-of-Care, Inc., Princeton, N.J., USA. The i-STAT® portable blood analysis system typically comprises Wi-Fi-enabled reader instruments that work in conjunction with single-use blood testing cartridges that contain sensors for various analytes. For further information on the i-STAT® portable blood analysis system, see http://www.abbottpointofcare.com/.

Analyzers, such as a self-contained disposable sensing device or cartridge and a reader or instrument, are further described in commonly owned U.S. Pat. No. 5,096,669 to Lauks, et al., the entirety of which is incorporated herein by reference. In operation, a fluid sample to be measured is drawn into a device and the device is inserted into the reader through a slotted opening. Data generated from measurements performed by the reader may be output to a display and/or other output device, such as a printer, or, as described in greater detail below, via a wireless network connection. The disposable device may contain sensing arrays and several cavities and conduits that perform sample collection, provide reagents for use in measurement and sensor calibration, and transport fluids to and from the sensors. Optionally, reagents may be mixed into the sample for testing. Sensing arrays in the device measure the specific chemical species in the fluid sample being tested. The electrochemical sensors are exposed to and react with the fluid sample to be measured generating electrical currents and potentials indicative of the measurements being performed. The electrochemical sensors may be constructed dry and when the calibrant fluid flows over the electrochemical sensors, the sensors easily "wet up" and are operational and stable for calibration and composition measurements. These characteristics provide many packaging and storage advantages, including a long shelf life. Each of the sensing arrays may comprise an array of conventional electrical contacts, an array of electrochemical sensors, and circuitry for connecting individual sensors to individual contacts. The electrical signals are communicated to a reader enabled to perform calculations and to display data, such as the concentration of the results of the measurement.

Although the particular order in which the sampling and analytical steps occur may vary between different point-of-care systems and providers, the objective of providing rapid sample test results in close proximity to a patient remains. The reading apparatus (e.g., i-STAT® or other wireless analyzer) may then perform a test cycle (i.e., all the other analytical steps required to perform the tests). Such simplicity gives the physician quicker insight into a patient's physiological status and, by reducing the time for diagnosis, enables a quicker decision by the physician on the appropriate treatment, thus enhancing the likelihood of a successful patient treatment.

In the emergency room and other acute-care locations within a hospital, the types of sample tests required for individual patients can vary widely. Thus, point-of-care systems generally offer a range of disposable devices configured to perform different sample tests, or combinations of such tests. For example, for blood analysis devices, in addition to traditional blood tests, including oxygen, carbon dioxide, pH, potassium, sodium, chloride, hematocrit, glucose, urea, creatinine and calcium, other tests may include, for example, prothrombin time (PT), activated clotting time (ACT), activated partial thromboplastin time (APTT), troponin, creatine kinase MB (CKMB), and lactate. Although devices typically contain between one and ten tests, it will be appreciated by persons of ordinary skill in the art that any number of tests may be contained in a device.

To illustrate examples of the need for different devices, a patient suspected of arrhythmia may require a device with a test combination that includes a potassium test, whereas a patient suspected of diabetes may require a device with a test combination that includes a glucose test. An emergency room will need to have sufficient inventory of both types of devices to ensure the supply meets the anticipated workload, while seeking to limit the economic cost associated with carrying an unnecessarily high inventory. Consequently, efficient communication of inventory status is another reason for implementing a secure wireless connection with the hospital network.

A given hospital may use numerous different types of test devices and test instruments at multiple point-of-care testing locations within the hospital. These locations can include, for example, an emergency room (ER), a critical care unit (CCU), a pediatric intensive care unit (PICU), an intensive care unit (ICU), a renal dialysis unit (RDU), an operating room (OR), a cardiovascular operating room (CVOR), general wards (GW), and the like. Other non-hospital-based locations where medical care is delivered, include, for example, MASH units, nursing homes, and cruise, commercial, and military ships. For all of these, establishing efficient communication between the wireless analyzer/point-of-care device and lab or computer that analyzes the data (e.g., LIS/HIS) via a secure wireless network may be essential.

Thus, in creating and maintaining an environment suitable for point-of-care sample testing (e.g., when a nurse performs sample tests at, or proximate to, the bedside of the patient), many of the forgoing problems associated with delay due to insecure sample transportation to a hospital laboratory for analysis must be eliminated. These problems can be eliminated by implementing secure wireless communication between a wireless analyzer, such as a point-of-care medical instrument, and a hospital network system (e.g., LIS or HIS). In addition, establishing secure wireless communication between a wireless analyzer and a hospital network system is beneficial in maintaining patient confidentiality as well as the confidentiality of associated medical information.

The following patents relating to point-of-care sample testing provide additional background and are incorporated herein by reference in their entireties: DISPOSABLE SENSING DEVICE FOR REAL TIME FLUID ANALYSIS to Lauks, et al., U.S. Pat. No. 5,096,669; WHOLLY MICROFABRICATED BIOSENSORS AND PROCESS FOR THE MANUFACTURE AND USE THEREOF to Cozzette, et al., U.S. Pat. No. 5,200,051; METHOD FOR ANALYTICALLY UTILIZING MICROFABRICATED SENSORS DURING WET-UP to Cozzette, et al., U.S. Pat. No. 5,112,455; SYSTEM, METHOD AND COMPUTER IMPLEMENTED PROCESS FOR ASSAYING COAGULATION IN FLUID SAMPLES to Opalsky, et al., U.S. Pat. No. 6,438,498; MICROFABRICATED APERTURE-BASED SENSOR to Davis, et al., U.S. Pat. No. 6,379,883; APPARATUS FOR ASSAYING VISCOSITY CHANGES IN FLUID SAMPLES AND METHOD OF CONDUCTING SAME to Davis, et al., U.S. Pat. No. 5,447,440; REUSABLE TEST UNIT FOR SIMULATING ELECTROCHEMICAL SENSOR SIGNALS FOR QUALITY ASSURANCE OF PORTABLE BLOOD ANALYZER INSTRUMENTS to Zelin, et al., U.S. Pat. No. 5,124,661; STATIC-FREE INTERROGATING CONNECTOR FOR ELECTRICAL COMPONENTS to Lauks, U.S. Pat. No. 4,954,087; REFERENCE ELECTRODE, METHOD OF MAKING AND METHOD OF USING SAME to Lauks, U.S. Pat. No. 4,933,048; and POINT-OF-CARE INVENTORY MANAGEMENT SYSTEM AND METHOD to Tirinato, et al., U.S. Pat. No. 7,263,501.

Oplasky, et al., U.S. Pat. No. 6,438,498 (the "'498 patent"), describes a computer system optionally including at least one infrared transmitter and/or infrared receiver for either transmitting and/or receiving infrared signals from a point-of-care blood testing instrument. Communications with such external devices—for example, the other components of the system—occur utilizing a communication port. For example, optical fibers and/or electrical cables and/or conductors and/or optical communication (e.g., infrared, and the like) and/or wireless communication (e.g., radio frequency (RF), and the like) can be used as the transport medium between an external device and a communication port. In addition to the standard components of the computer, the computer also optionally includes an infrared transmitter and/or infrared receiver. Infrared transmitters are optionally utilized when the computer system may be used in conjunction with one or more of the processing components/stations that transmits/receives data via infrared signal transmission. Instead of utilizing an infrared transmitter or infrared receiver, the computer system optionally uses a low power radio transmitter and/or a low power radio receiver. The low power radio transmitter transmits the signal for reception by components of the production process and receives signals from the components via the low power radio receiver. However, the '498 patent does not address the issue of establishing a secure Wi-Fi connection to a hospital network. Although infrared technology is still used in modern applications, it suffers from a number of limitations. A first limitation is the inability of an infrared signal to penetrate walls, thus restricting transmission to a single room. A second limitation is that many indoor environments can experience infrared background radiation (e.g., from sunlight and indoor lighting). This background radiation can act as noise to an infrared receiver, necessitating the use of higher power transmitters while further limiting the range.

U.S. Pat. No. 6,845,327 (the "'327 patent") entitled POINT-OF-CARE IN-VITRO BLOOD ANALYSIS SYSTEM to Lauks describes devices for performing in-vitro diagnostic chemical analyses at multiple distributed locations within a medical institution that involve a wireless network. However, the '327 patent does not address the issue of establishing a secure Wi-Fi connection to a hospital network.

U.S. Pat. No. 7,041,468 (the "468 patent") entitled BLOOD GLUCOSE TRACKING APPARATUS AND METHODS to Drucker, et al., describes a measurement module for glucose testing including a glucose testing measurement module housing, a test strip receptacle formed in the housing, and a connector portion formed in the housing and shaped to permit mechanical, removable attachment of the housing to a handheld processing device, handheld computer, PDA, mobile phone, or wireless processing device. Electronics are provided either in the measurement module or in the handheld processing device for determining the amount of glucose present in a sample of body fluid when a test strip is positioned in the receptacle and the fluid is placed on the test strip, and for communicating the glucose amount to the processing device via the connector portion. However, the '468 patent does not address the issue of establishing a secure Wi-Fi connection to a hospital network.

U.S. Pat. No. 7,235,213 (the "'213 patent") entitled SYSTEM FOR PERFORMING BLOOD COAGULATION ASSAYS AND MEASURING BLOOD CLOTTING TIMES to Mpock, et al., describes a system for performing a blood coagulation assay having (i) a reaction chamber; (ii) at least one movable member configured to mix contents of the reaction chamber; (iii) a sensor configured to detect the presence of a blood clot formed in the reaction chamber; and (iv) a timer that measures an interval of time between when a blood sample is received into the reaction chamber and when the sensor detects the blood clot formed in the reaction chamber. The timer is an instrument that would desirably be able to communicate patient results for a prothrombin time (PT) test securely to a hospital wireless network. However, the '213 patent does not address the issue of establishing a secure Wi-Fi connection to a hospital network.

Two popular types of wireless technology standards available are Bluetooth® and the Institute of Electrical and Electronic Engineering's (IEEE) 802.11 standards ("Wi-Fi"). Bluetooth® is an open specification delivering short-range radio communication between electrical devices that are equipped with Bluetooth® chips. When two Bluetooth®- enabled devices are within communication range (currently about 10 meters), they send each other a unique ID to identify one another. This ID is used to determine the type of information to be shared and the level of functionality that could occur between the two devices. However, Bluetooth® is not designed for long-distance communication, e.g., greater than about 10 meters, but rather as a means for providing connections between mobile computing devices or between a mobile computer device and a hub. To increase operating range, Wi-Fi, which has a larger operating range (currently up to about 300 meters) may be used. Wi-Fi is an extension of the wired Ethernet and uses the same principles as its wired counterpart, thus providing its users with high-speed, reliable connections to a network. Notably, U.S. Pat. No. 5,487,069 entitled WIRELESS LAN to O'Sullivan, et al., the entirety of which is incorporated herein by reference, describes a wireless LAN, a peer-to-peer wireless LAN, a wireless transceiver, and a method of transmitting data, all of which are capable of operating at frequencies in excess of 10 GHz and in multipath transmission environments. In the LANs, the mobile transceivers are each connected to, and powered by, a corresponding portable electronic device with computational ability.

With respect to the establishment of communication with a secure wireless network, it may be typical for the user of a wireless device to enter (e.g., via the combination of a keyboard, display and mouse, touch pad, touch screen, or equivalents) multiple networking parameters (e.g., IP address, network address, network name (also referred to as Service Set Identifier—SSID), and network security settings such as authentication, encryption, network keys and username/password combination) related to the wireless infrastructure and, in certain cases, also download network certificates to the device for authentication purposes.

Unfortunately, the existing methods of connection and authentication requiring input from the user can be both cumbersome and impractical. For example, the number of point-of-care instruments requiring a connection can typically range from 5 to 100 instruments, usually spread over multiple locations within a hospital (ER, ICU, OR, etc). Furthermore, these devices may not include a convenient input mechanism (e.g., a keyboard, actual or virtual, or touch pad). In general, point-of-care blood testing systems (e.g., glucose meters, coagulation meters, and multiple blood testing cartridge instruments) are designed as customized, proprietary devices without general computer features. Thus, the need exists for improved processes for securely networking one or more wireless analyzers to a hospital network without the need for an operator or user to engage in manual initiation steps on or through the analyzers or other instruments.

SUMMARY OF THE INVENTION

The present invention addresses the various limitations in the prior art by providing improved processes for securely networking one or more wireless analyzers with Wi-Fi without the need for an operator or user to engage in manual initiation steps on or through the instrument. In certain embodiments of the present invention, the one or more wireless analyzers are configured to perform as a Wireless Access Point (WAP) and the authentication process of the one or more analyzers for securely networking the one or more wireless analyzers with Wi-Fi may be initiated remotely via a network controller using a computing device (e.g., a computer) and a wireless network link. The present application discloses a system and method for initiating and maintaining secure wireless communication between a wireless analyzer and a hospital network (e.g., a hospital Wi-Fi network connected to an LIS, HIS and/or other computer). The present disclosure addresses the various limitations in the prior art by providing a secure method for networking these wireless analyzers with a Wi-Fi network without the need for an operator or user to engage in manual initiation steps on or through the wireless analyzer. In the present invention, the one or more wireless analyzers are configured to perform as a WAP and the authentication process may be initiated remotely via a network controller using a computing device and a wireless network link.

In a first embodiment, the present invention is directed to a system for establishing a wireless network in point of care testing. The system comprises: (i) a wireless analyzer configured to authorize wireless access to the wireless analyzer, and read a patient health parameter; (ii) a computing device configured to obtain the wireless access with said wireless analyzer using a wireless network identifier, and communicate access credentials to said wireless analyzer via said wireless access; and (iii) a primary wireless network configured to communicate with said wireless analyzer, authenticate a secure connection with the wireless analyzer using the access credentials, and receive the patient health parameter via the secure connection.

In a second embodiment, the present invention is directed to a method of connecting a wireless analyzer to a primary wireless network. The method comprises the steps of: (i) receiving at the wireless analyzer a request for wireless access to the wireless analyzer from at least one computing device, wherein the wireless analyzer is configured to read a patient health parameter, and the at least one computing device is configured to use a wireless network identifier identifying the wireless analyzer to send the request for the wireless access; (ii) authorizing the wireless access to the wireless analyzer; (iii) receiving at the wireless analyzer access credentials for the primary wireless network from the at least one computing device; (iv) terminating the wireless access with the at least one computing device; and (v) authenticating a secure connection between the wireless analyzer and the primary wireless network using the access credentials.

In a third embodiment, the present invention is directed to a wireless analyzer enabled for secure communication with a primary wireless network comprising: (i) a display; (ii) an input device; (iii) a sensing apparatus for detecting a patient health parameter; (iv) an antenna; (v) a wireless access point (WAP) module configured to establish a wireless connection with the wireless analyzer from a computing device using a wireless network identifier, and obtain at least one access credential for the primary wireless network from the computing device; and (vi) a host processor configured to authenticate a secure wireless connection with the primary wireless network using the at least one access credential.

In a fourth embodiment, the present invention is directed to a computer program product comprising a computer usable storage medium having readable program code embodied in the storage medium. The computer program product includes at least one component operable to: (i) receive at a wireless analyzer a request for wireless access to the wireless analyzer from at least one computing device, wherein the wireless analyzer is configured to read a patient health parameter, and the at least one computing device is configured to use a wireless network identifier identifying the wireless analyzer to send the request for the wireless access; (ii) authorize the wireless access to the wireless analyzer; (iii) receive at the wireless analyzer access credentials for a primary wireless network from the at least one computing device; (iv) terminate the wireless access with the at least one computing device; and (v) authenticate a secure connection between the wireless analyzer and the primary wireless network using the access credentials.

The wireless analyzer may be further configured to perform a function via said primary wireless network comprising: (i) communicating location; (ii) receiving and displaying a custom message; (iii) communicating and installing software updates; (iv) communicating print requests with a printer in communication with said primary wireless network; (v) communicating battery level; (vi) communicating dynamic display information with a computer in communication with said primary wireless network; (vii) synchronizing time with a computer in communication with said primary wireless network; (viii) provide network access to another wireless analyzer; or (ix) combinations thereof.

In some embodiments, the secure connection comprises a Secure Sockets Layer (SSL) connection, a Transport Layer Security (TLS) connection, an SSL/TLS connection, or combinations thereof.

In some embodiments, the primary wireless network may comprise a hospital wireless network in communication with a laboratory information system and/or hospital information system.

In some embodiments, a wireless analyzer may communicate blood test, e.g. potassium, glucose, prothrombin time, patient data between a wireless analyzer and said primary wireless network. The wireless analyzer may further receive a blood testing cartridge with at least one sensor, prothrombin time test device, and/or a glucose test strip.

In some embodiments, a wireless analyzer may receive data communicated from the primary wireless network, wherein the data comprises: (i) a software upgrade; (ii) an instrument calibration coefficient; (iii) an instrument self-validation protocol; (iv) an instrument self-testing protocol; or (v) a combinations thereof.

BRIEF DESCRIPTION OF THE DRAWINGS

The present invention will be better understood in view of the appended non-limiting figures, in which:

FIG. 1b is a diagram showing connection of a wireless analyzer to a primary wireless network after receiving settings and certificates from a computing device over a wireless network;

FIG. 2 is a flow diagram illustrating a process of initiation and creation of a secure communication link between a wireless analyzer and a primary wireless network;

FIG. 4c is a diagram showing a wireless analyzer acting as a router for another wireless analyzer.

DETAILED DESCRIPTION OF THE INVENTION

Figure 1A:
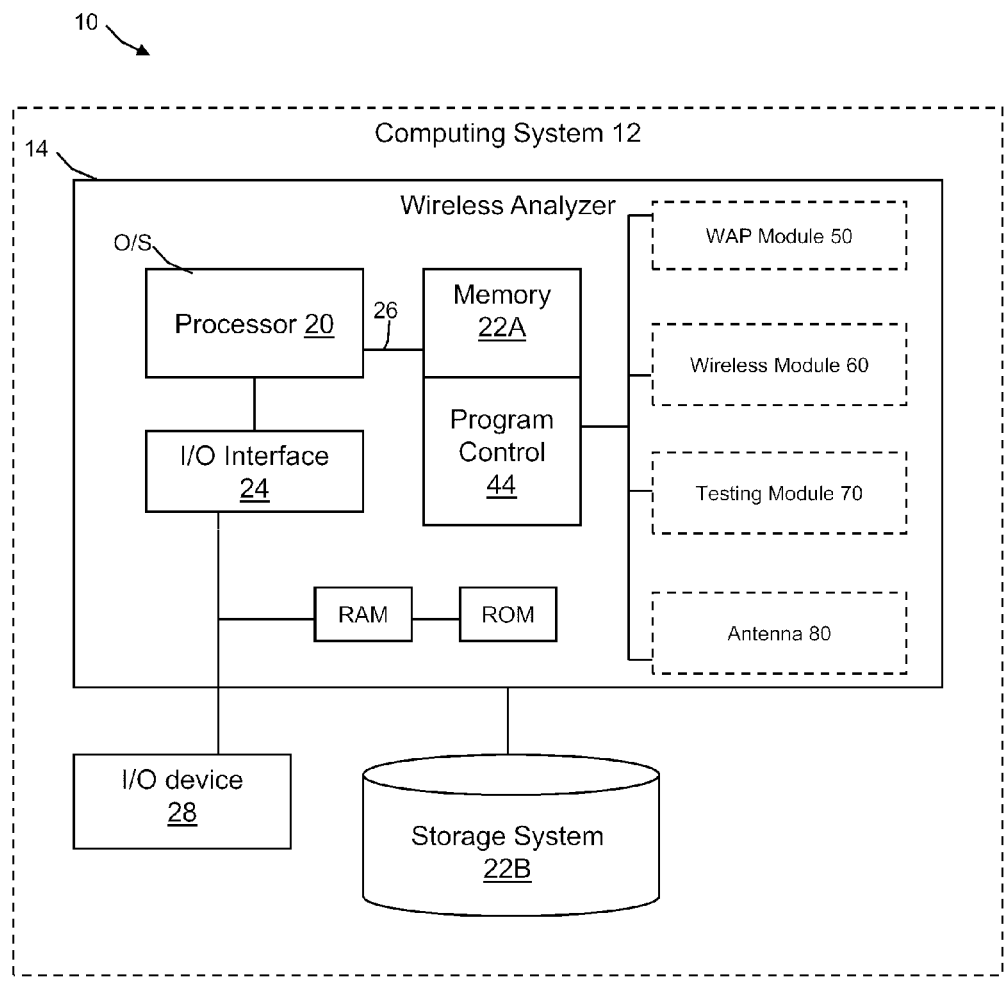
FIG. 1a is an illustrative diagram of an external environment for implementing the invention in accordance with aspects of the invention.

The term "access credentials," as used herein, refers to any information required to gain access to a secure network, including, but not limited to, wireless settings, network access certificates, encryption keys, and authentication credentials.

The terms "communicate" and "communicating," as used herein, refers to bi-directional transmitting, or otherwise conveying, data from a source to a destination and delivering data to a communications medium, system, channel, network, device, wire, cable, fiber, circuit, and/or link to be conveyed to a destination.

The terms "coupled," "coupled to," and "coupled with," as used herein, each refer to a relationship between or among two or more devices, apparatus, files, circuits, elements, functions, operations, processes, programs, media, components, networks, systems, subsystems, and/or means, constituting any one or more of (i) a connection, whether direct or through one or more other devices, apparatus, files, circuits, elements, functions, operations, processes, programs, media, components, networks, systems, subsystems, or means; (ii) a communications relationship, whether direct or through one or more other devices, apparatus, files, circuits, elements, functions, operations, processes, programs, media, components, networks, systems, subsystems, or means; and/or (iii) a functional relationship in which the operation of any one or more devices, apparatus, files, circuits, elements, functions, operations, processes, programs, media, components, networks, systems, subsystems, or means depends, in whole or in part, on the operation of any one or more others thereof.

The term "database," as used herein, refers to an organized body of related data, regardless of the manner in which the data or the organized body thereof is represented. For example, the organized body of related data may be in the form of one or more of a table, a map, a grid, a packet, a datagram, a frame, a file, an e-mail, a message, a document, a report, a list, or in any other form.

The terms "EAP" and "EAP-TLS", as used herein, each refer to a universal authentication framework used in wireless networks. EAP (Extensible Authentication Protocol) refers to an authentication framework frequently used in wireless networks and Point-to-Point connections—defined in RFC 3748 and updated by RFC 5247. EAP-TLS (Extensible Authentication Protocol-Transport Layer Security) refers to a standard supported in wireless communications to secure communications using public key infrastructure (typically using certificates).

The term "health-care data", as used herein, refers to any data representing a health parameter, physiological parameter, or other patient data generated, collected, or provided by a wireless analyzer.

The term "network", as used herein, refers to both networks and inter-networks of all kinds, including the Internet, but is not limited to any particular network or inter-network.

The term "portable device", as used herein, refers to a device capable of being carried by or on a person, including without limitation, wireless analyzer, a cellular telephone, a personal digital assistant ("PDA"), a Blackberry® device, a radio, a television, a game system, a notebook computer, a laptop/desktop computer, a GPS device, a personal audio device (such as an MP3 player or an iPod™ device), a DVD player, a two-way radio, a personal communications device, a telematics device, a remote control device, a wireless headset, a wristwatch, a portable data storage device (e.g., Thumb™ drive), a camera, or a recorder, as well as any devices combining any of the foregoing or their functions.

The term "processor", as used herein, refers to processing devices, apparatus, programs, circuits, components, systems, and subsystems, whether implemented in hardware, tangibly embodied software, or both, and whether or not programmable. The term "processor" as used herein includes, but is not limited to, one or more computers, hardwired circuits, signal modifying devices and systems, devices and machines for controlling systems, central processing units, programmable devices and systems, field-programmable gate arrays, application-specific integrated circuits, systems on a chip, systems comprising discrete elements and/or circuits, state machines, virtual machines, data processors, processing facilities, and combinations of any of the foregoing.

The terms "Pre-Shared Key" and "PSK," as used herein, refers to a shared secret password between a wireless device and a network. For example, a secure network often requires a PSK before granting a wireless device access into the network.

The term "RC4," as used herein, refers to a software stream cipher used in protocols such as SSL and WEP.

The terms "Service Set Identifier" and "SSID," as used herein, refers to a name that identifies a particular wireless local area network (WLAN)

The terms "Temporal Key Integrity Protocol" and "TKIP," as used herein, refers to a security protocol for wireless networking. TKIP security protocol allows wireless devices and a network exchange messages in a secure manner (e.g., message integrity check, protects against attacks). TKIP security protocol may use RC4 as an encryption method.

The terms "Wireless Access Point" and "WAP," as used herein, refers to a device that allows wireless devices to connect to a wired network using Wi-Fi, Bluetooth® or related standards The term "WPA," as used herein, refers to WPA-Personal and/or WPA-Enterprise. WPA-Personal typically uses PSK for encryption and TKIP for security whereas WPA-Enterprise typically uses TKIP for security with EAP.

The term "WPA2," as used herein, refers to WPA2-Personal and/or WPA2-Enterprise. WPA2-Personal typically uses AES encryption and PSK for security, whereas WPA2-Enterprise typically uses AES encryption and EAP for security.

The term "wireless analyzer," as used herein, refers to a wireless enabled device enabled to read at least one patient health parameter and may include, but is not limited to: point-of-care test instruments; the i-STAT® portable blood analysis system; and other wireless-enabled portable blood analysis instruments, including (i) ones that receive a blood testing cartridge with at least one sensor; (ii) ones in which the portable blood analysis instrument is a glucose meter and receives a glucose test strip; and (iii) ones in which the portable blood analysis instrument is a blood coagulation meter and receives a prothrombin time-test device.

The terms "a wireless analyzer" or "wireless analyzer," as used herein, refers to one or more wireless analyzers and should not be construed to only mean a single wireless analyzer.

The secure wireless system of the present invention may be coupled to, or integrated with, a wireless analyzer. The present invention will be described primarily in the context of wireless analyzers, including, for example, the i-STAT® portable blood analysis system, a type of point-of-care device; however, it should be appreciated that a person having ordinary skill in the art would appreciate that the present application can be applied to any portable device, including any wireless-enabled, processor-based, portable device.

To enable wireless communication, a WAP module and/or a wireless module may be embedded within or incorporated with an analyzer to create a wireless analyzer that may enable the wireless analyzer to perform as a WAP and wirelessly communicate test results from the wireless analyzer to a database, central data station and/or primary wireless network using a variety of wireless connectivity methods within the Wi-Fi standard, e.g., via the IEEE 802.11 standard. A wireless module and an access point may be configured with a PSK, AES, EAP, and/or TKIP. Regardless of the type of WAP module and/or wireless module used in the wireless analyzer, the wireless analyzer may offer the user the option to activate or deactivate (e.g., turn on/off) the WAP module and/or the wireless module or wireless functionality. Furthermore, the wireless analyzer may be in communication with a barcode reader using either the wireless module or the serial port. Here the barcode reader can be used to scan a barcode on the test device, e.g. a blood testing cartridge where the code identifies the cartridge type, expiration date etc., scan a barcode on a patient's wrist, scan a barcode on the badge of a user, e.g. nurse and physician, and the like.

A primary purpose of enabling the wireless analyzer to perform as a WAP is to enable secure communication of access credentials from a computing device to the wireless analyzer so that the wireless analyzer may obtain authentication and gain access to a hospital wireless network (e.g., via Wi-Fi-IEEE 802.11), e.g., a primary wireless network. Generally speaking, Network Access Control (NAC) systems use various methods of access credentials and access authentication methods, including security certificates. Such certificate-based authentication systems rely on trusted certificate authorities for their credibility. For example, EAP-Transport Layer Security (EAP-TLS) is a widely used standard for wireless access authentication. When EAP-TLS is used with certificates, both the client and the server may use one or more certificates to verify the identities of each party. In some embodiments, PEAP-EAP-MS-CHAPv2 may be used as the authentication method. Specifically, PEAP-EAP-MS-CHAPv2 is a password-based user authentication method that uses TLS with server certificates. During PEAP-EAP-MS-CHAPv2 authentication, the computing device supplies a certificate to validate its identity to the wireless analyzer. Alternatively, PEAP-EAP-TLS, which provides strong security and uses a PKI with certificates, may be used. The wireless analyzer may also be enabled to support: WEP 64, WEP 128, WEP with transactional keys, WPA1 with pre-shared keys, WPA2 with pre-shared keys, EAP-TLS, EAP-TTLS, PEAP-MSCHAP.

In some embodiments, SSL, TLS, PSK, WiFi Protected Access (WPA), WPA1, WPA2, and/or WPA-Enterprise (WPA-802.1x) systems may be used to create the secured communication path between the computing device and the wireless analyzer. In accordance with aspects of the invention, SSL, TLS, PSK, WPA, WPA1, WPA2, and/or WPA-Enterprise (WPA-802.1x) protocols provide a secure digital communication link between the computing device comprising access credentials and the wireless analyzer. Similarly, SSL, TLS, PSK, WPA, WPA1, WPA2, and/or WPA-Enterprise (WPA-802.1x) secured communication technology may be further used to provide secure Web browsing to the wireless analyzer once a connection has been established between the wireless analyzer and a secure Wi-Fi network.

System Environment

The present invention may be embodied as a system, method or computer program product. The present invention may take the form of a hardware embodiment, a software embodiment or a combination of software and hardware. Furthermore, the present invention may take the form of a computer program product embodied in any tangible storage of expression having computer-usable program code embodied in the medium. The computer-usable or computer-readable medium may be any medium that can contain, store, or communicate, for use by or in connection with the instruction execution system, apparatus, or device.

Any combination of one or more computer readable medium(s) may be utilized. The computer readable storage medium may be, for example, but not limited to, an electronic, magnetic, optical, electromagnetic, infrared, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

FIG. 1a shows an illustrative environment 10 for managing the processes in accordance with the invention. The environment 10 includes a computing system 12 that can perform the processes described herein. The computing system 12 includes a wireless analyzer 14, which can be resident on a network infrastructure. The wireless analyzer 14 includes a host processor 20, a memory 22A, an I/O interface 24, and a bus 26. In addition, the wireless analyzer 14 includes random access memory (RAM), a read-only memory (ROM), and an operating system (O/S).

The wireless analyzer 14 may be in communication with the external I/O device/resource 28 and the storage system 22B. The I/O device 28 can comprise any device that enables an individual to interact with the wireless analyzer 14 (e.g., user interface) or any device that enables the wireless analyzer 14 to communicate with one or more other wireless analyzers using any type of communications link.

The host processor 20 executes computer program code (e.g., program control 44), which can be stored in the memory 22A and/or the storage system 22B. While executing the computer program code, the host processor 20 can read and/or write data to/from memory 22A, storage system 22B, and/or I/O interface 24. The program code executes the processes of the invention such as, for example, translating a text-based command assigned to a service command configured to control a service, into the service command.

The wireless analyzer 14 may include a WAP module 50, a Wireless module 60, and a Testing module 70 that may be portions of the computer program code and/or implemented as hardware components. The WAP module 50, the Wireless module 60, and the Testing module 70 perform the processes of the invention, for example, the WAP module 50, the Wireless module 60, and the Testing module 70 may be configured to impart the functionality of the wireless analyzer 14 including: (i) as a WAP including the functionality of performing as a router during wireless communication, (ii) as a transceiver for communicating data through a wireless network, and (iii) as a analyzer for at least one patient health parameter, as described in detail below, and each can be its own dedicated special processor or combination thereof. Additionally the wireless analyzer 14 may include an external or internal antenna 70 for sending and/or receiving data wirelessly.

FIG. 1b illustrates an embodiment of the present invention embodied in system 100A wherein at least one wireless analyzer 102 (e.g., the wireless analyzer 14 previously described with respect to FIG. 1a) is in communication with a primary wireless network 108 (e.g., a Wi-Fi network typically found in hospital and/or medical delivery location). For the sake of simplicity, only one wireless analyzer 102 is shown in FIG. 1b; however, it would be understood to one having ordinary skill in the art that one or more wireless analyzers 102 may be used in system 100A.

The system may comprise a wireless analyzer 102, a computing device 104, (e.g., a computer) enabled to communicate with the wireless analyzer 102 using a wireless network 106, and a primary wireless network 108. The primary wireless network 108 may comprise, for example, an authentication server 110, laboratory information systems (LIS) and/or hospital information systems (HIS) 112, hospital wireless access points 114A, 114B, and a printer/printer server 126. Primary wireless network 108 may also be in communication with a database and/or a central data station (CDS) 124 used to store data and/or run data management software. Authentication server 110 may be responsible for verifying the access credentials (e.g., certificates) of a wireless analyzer 102 and permitting, if the access credentials are valid, access to one or more hospital networks, systems, and computers (e.g., one or more LIS/HIS networks 112, databases, printers 126, etc.) in communication with the primary wireless network 108. Authentication server 110 may use, for example, RADIUS (Remote Authentication Dial In User Service) functionality. RADIUS is a networking protocol for providing centralized authentication and may be used to authorize wireless analyzer's 102 access to the primary wireless network 108. The access points 114A, 114B may transfer the authentication responsibility to RADIUS when running in EAP mode. The secure connection 122 may also be used to communicate and update user/patient lists and/or user/patient information between the wireless analyzer 102 and central data station 124 and/or LIS/HIS networks 112 via the primary wireless network 108. The primary wireless network 108 may also be in communication with one or more printers 126, allowing a wireless analyzer 102 to easily print data, results and other reports using printer 126.

For example, one or more LIS/HIS networks 112 may receive health-care data and/or other measurement data from the wireless analyzer 102 and manipulate the data to generate results and/or values that provide patient state of health parameters to a patient caretaker (e.g., signs of anemia, dehydration, sepsis, myocardial infarction, congestive heart failure, diabetes, hypoxia, renal insufficiency and the like). The one or more hospital wireless access points 114A, 114B are responsible for sending and receiving data between the primary wireless network 108 and a wireless analyzer 102 (e.g., via Wi-Fi/IEEE 802.11).

To securely transmit healthcare data from the wireless analyzer 102 to the primary wireless network 108, a wireless analyzer 102 is configured to function as a WAP to obtain access credentials to the primary network 108. For example, the WAP module 50 may be configured to enable the wireless analyzer 102 to function as a WAP by broadcasting 118 an SSID and/or by being enabled to receive an SSID and establish a wireless network 106. The established wireless network 106 enables the computing device 104 to provide the wireless analyzer 102 with one or more access credentials for the primary wireless network 108. The computing device 104, which is enabled to communicate wirelessly, may include the one or more access credentials and, in certain embodiments, computing device 104 may generate and provide one or more dynamic authentication credentials that change at given time intervals. For example, RSA, the security division of EMC Corporation (http://www.rsa.com/node.aspx?id=1156), provides additional suitable secure data, compliance, SIM, SEM, SIEM, PCI, consumer identity, two-factor authentication, and other security solutions that may be incorporated with computing device 104.

In accordance with aspects of the invention, as a result of the computing device 104 being wirelessly connected to the wireless analyzer 102 over the wireless network 106, the computing device 104 may communicate 120 the one or more access credentials to the wireless analyzer 102 using a secure connection over the wireless network 106. For example, prior to communicating 120 the access credentials, the computing device 104 may verify the identity of the wireless analyzer 102 using identifiers (e.g., preset configurations, device name, device ID, previous communications, etc.). The secure connection over the wireless network 106 is temporary and used primarily for the purpose of initiating a connection between the wireless analyzer 102 and the primary network 108. The secure wireless connection between the computing device 104 and the wireless analyzer 102 may be a secure connection (e.g., SSL, TLS, SSL/TLS, PSK, WPA, WPA1, WPA2, WPA-Enterprise (WPA-802.1x), and/or any other cryptographic or encryption protocol connection). In certain embodiments, the secure wireless connection between the computing device 104 and the wireless analyzer 102 may be Bluetooth®. The access credentials from the computing device 104 may be communicated to the wireless analyzer 102 via the secure wireless connection and, once the transfer is completed, the secure wireless connection may be closed.

Using one or more access credentials received from computing device 104, the wireless analyzer 102 may authenticate (preferably automatically authenticate) a secure connection 122 between the wireless analyzer 102 and the primary wireless network 108 allowing the wireless analyzer 102 to operate securely within the hospital Wi-Fi network 108. During this period, data may be communicated between the wireless analyzer 102, the primary wireless network 108, the one or more LIS/HIS Networks 112, and/or any other computer/network/system in communication with the primary wireless network 108. Termination of the secure connection 122 may be set in accordance with the user's preferences. For example, termination may require the user to prompt for a termination (e.g., a log-out button); termination may occur automatically once a predetermined time duration has elapsed (e.g., measured from connection time); and/or the connection may time out and terminate due to inactivity (e.g., if data transfer, input or measurement has not occurred within a set time period). In the event of inactivity, a warning or other indicator may be displayed allowing the user to cancel the termination and maintain communication. Failure to respond to the warning or other indicator within a preset period of time (e.g., 60 seconds) may lead to immediate termination of the connection.

Figure 1C:
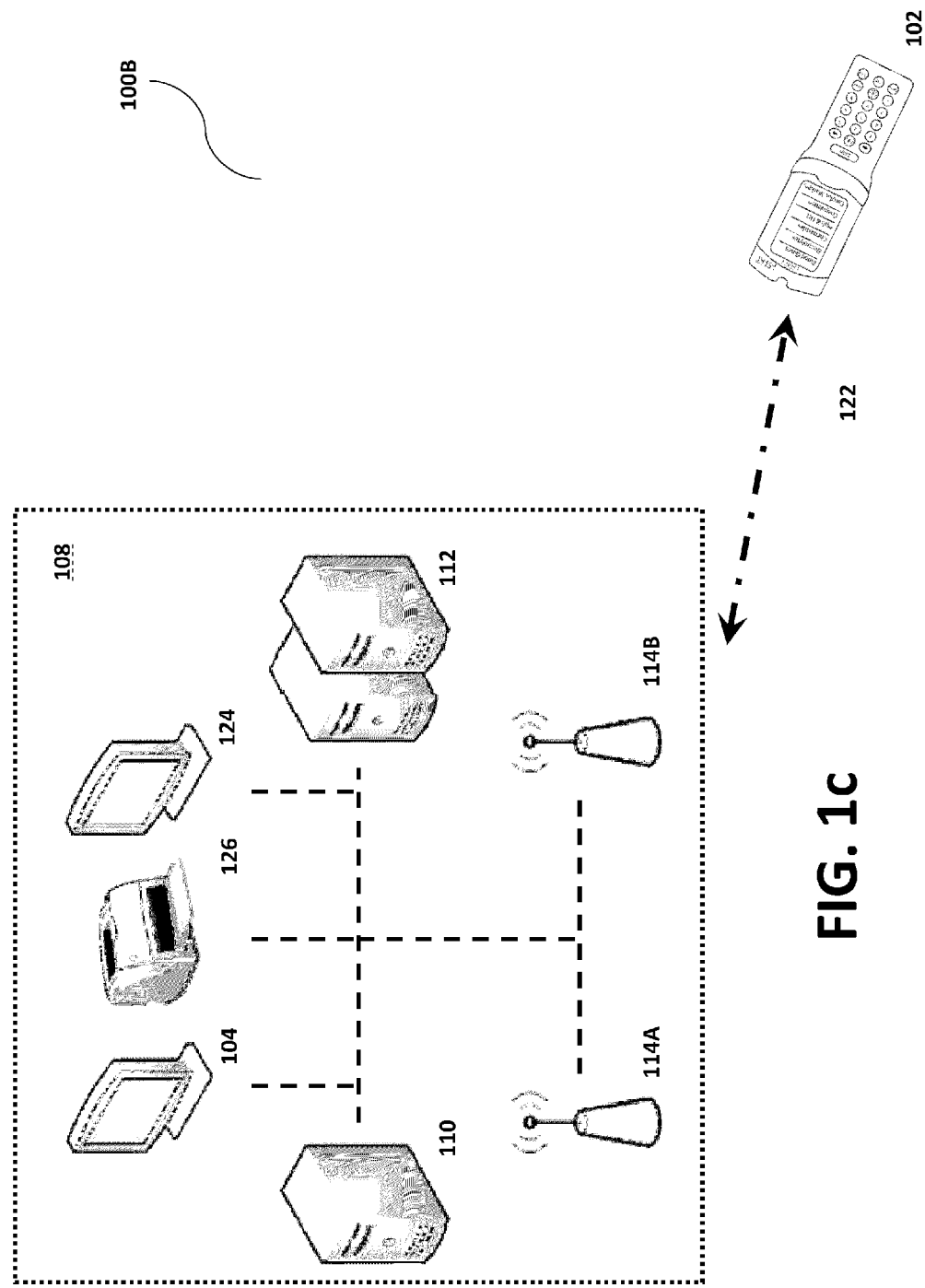
FIG. 1c is a diagram showing connection of a wireless analyzer to a primary wireless network after receiving settings and certificates from a network in communication with the primary wireless network.

FIG. 1c illustrates another embodiment of the present invention wherein a wireless analyzer 102 is in communication with a primary wireless network 108 (e.g., a wireless network typically in a hospital or medical delivery location). The system 100b operates in a similar manner as system 100a but illustrates that the computing device 104 comprising the access credentials may be in communication with the primary wireless network 108. According to FIG. 1c, the wireless analyzer 102 may function as a WAP and use a wireless connection with the computing device 104 for receiving the one or more access credentials, much as described above with respect to FIG. 1b.

As indicated above, the primary wireless network 108 may be a hospital wireless network that may be in communication with an LIS, HIS, database, and/or other services or networks.

In some embodiments, this secure wireless communication system may be used for a number of purposes, including, but not limited to, transmitting blood analysis patient data (both the blood test results and patient identification) from the wireless analyzer 102 to the LIS by way of the primary wireless network 108. In some embodiments, the wireless analyzer 102 can also transmit other data including, but not limited to, time and date, user identification, instrument calibration coefficients, instrument self-validation test results, instrument self-testing results, entered patient information (e.g., patient name or associated patient number, age, sex, allergies, patient temperature, symptoms, etc.), or combinations thereof.

Flow Diagram

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions, which execute on the computer or other programmable apparatus provide processes for implementing the functions/acts specified in the flowchart and/or block diagram block or blocks.

Figure 3:
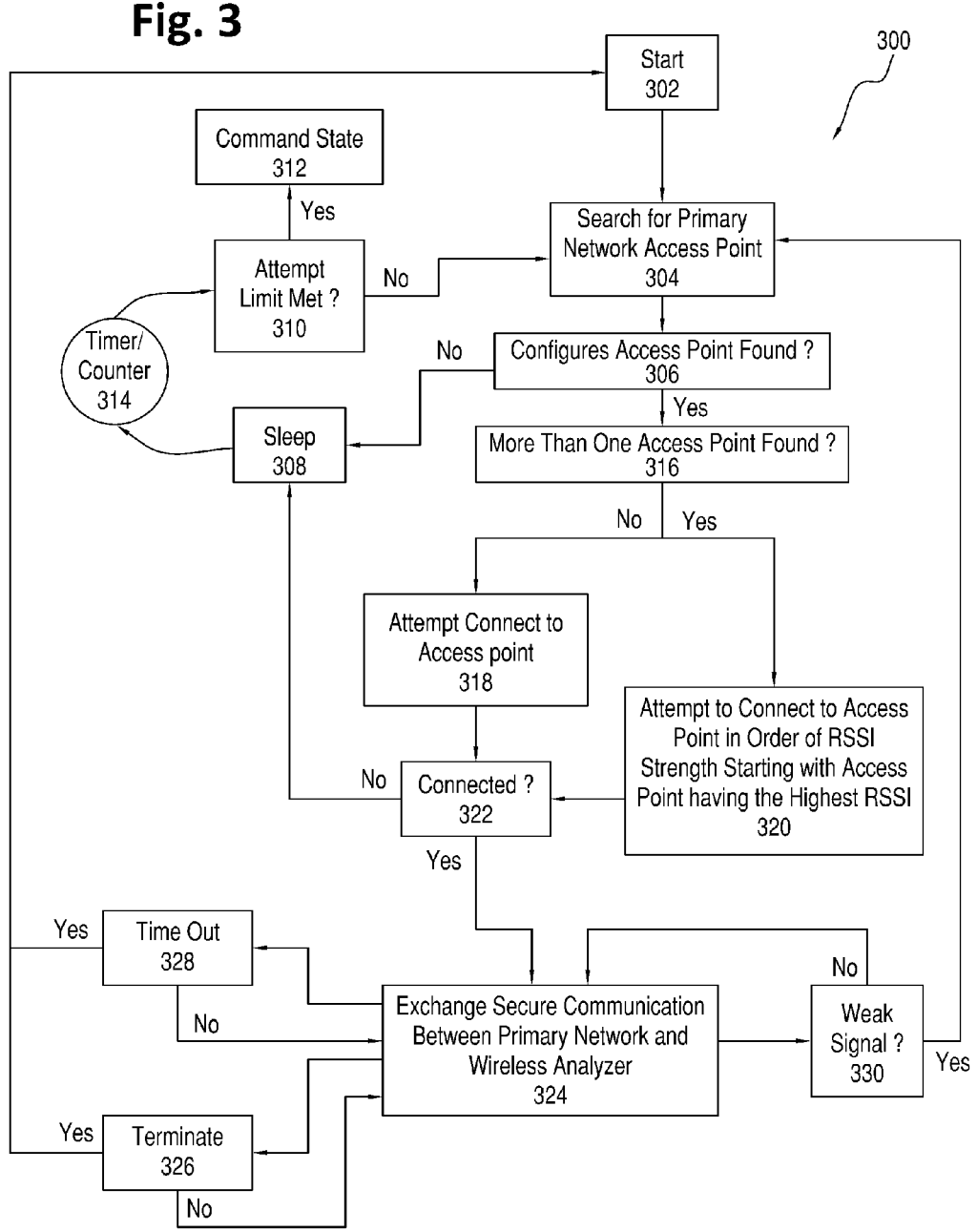
FIG. 3 is a flow diagram illustrating a process of establishing a communication link between a wireless analyzer and a primary wireless network.

FIGS. 2 and 3 show exemplary flows for performing aspects of the present invention. The steps of FIGS. 2 and 3 may be implemented in the environment and/or systems of FIGS. 1a, 1b, 1c, 4a, 4b, and 4c, for example. The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

FIG. 2 is a flow diagram illustrating a process of initiation and creation of a secure communication link between a wireless analyzer and a primary network. In embodiments, setup 201 may be prompted by a user (e.g., using a "setup" button/key) or by an "autosetup" process that executes automatically default settings or instructions when the wireless analyzer is activated. In accordance with aspects of the invention, the host processor 20 (as discussed above with respect to FIG. 1a) may be configured to activate the WAP module 50 using the settings or instructions. For example, the setting or instructions may comprise configuring the wireless analyzer to: (i) authorize wireless access from any computing device (e.g., a computer), (ii) authorize wireless access from one or more specified computing devices according to a specified password, and/or (iii) automatically authorize wireless access from one or more specified computing devices.

Initiation 202 may be prompted by the user (e.g., using a "log-on" or "connect" button/key) or by an "autorun" process that executes automatically when the wireless analyzer is activated. The initiation 202 may comprise the wireless analyzer using WAP hardware and/or software (e.g., the WAP module 50) to broadcast a WiFi SSID that is searchable as an available WiFi network 204 by a WiFi enabled computing device to establish a secure wireless connection (e.g., using SSL, TLS, PSK, WPA, WPA1, WPA2, WPA-Enterprise (WPA-802.1x), or any other cryptographic or encryption protocol connection) between the wireless analyzer and the computing device for communication of, for example, one or more primary wireless network access credentials. In embodiments, the wireless analyzer may not broadcast the WiFi SSID.

In embodiments, the initiation 202 may comprise the wireless analyzer using WAP hardware and/or software to receive a request to establish a wireless connection using the WiFi SSID from the computing device. For example, the WiFi SSID may be received by the computing device via the broadcast of the WiFi SSID from the wireless analyzer and/or input into the computing device (e.g., a user may input the WiFi SSID or a server may present the WiFi SSID to the computing device). Subsequently, the computing device may use the WiFi SSID to communicate a request for wireless connection to the wireless analyzer in order to establish a wireless connection with the wireless analyzer. In accordance with aspects of the invention, the WiFi SSID may be a known SSID, a SSID comprised from a unique name, or dynamically generated. The unique name for the SSID may be comprised of a media access control (MAC) address of the wireless analyzer, a serial number of the wireless analyzer, or any combination thereof.

In embodiments, the initiation 202 may comprise the wireless analyzer using WAP hardware and/or software to function as a dynamic host configuration protocol (DHCP) server. For example, the wireless analyzer may be configured automatically to wirelessly communicate with the computing device, eliminating the need for intervention by a network administrator. In accordance with aspects of the invention, the wireless analyzer may be configured to send network IP parameters to the computing device, and the computing device may be configured to receive the network IP parameters. The network IP parameters may comprise, for example, IP address, subnet mask, gateway, and domain name system (DNS). The network IP parameters may then be used subsequently by the computing device to establish the secure wireless connection with the wireless analyzer.

In embodiments, the computing device may create, or prepare to communicate, primary wireless network access credentials (e.g., a session encryption key) 206. For added security, the wireless network access credentials would typically comprise a random number, or an alphanumeric string, created for a single session. Once communication between the computing device and wireless analyzer has been established 208, using public key cryptography and/or encryptology, the computing device may securely communicate the session key to the wireless analyzer using the wireless network 210. For example, the computing device may communicate the session key to the wireless analyzer using simple network management protocol (SNMP). The session encryption key, which is known by the wireless analyzer, the computing device and the primary wireless network, may be used to encrypt any digital traffic sent between the devices (e.g., between the primary wireless network and wireless analyzer, however it may also be used to encrypt communication between the wireless analyzer and computing device). As the session encryption key is preferably a symmetric encryption key, the wireless analyzer may then use that same session key to decrypt digital traffic received from the primary wireless network.

At some point during the communication between the wireless analyzer and the computing device 208, the computing device may determine that the wireless analyzer should be provided with the requested access credentials for primary wireless network access, the computing device may then use the secure connection to transmit the primary network access credentials to the wireless analyzer 210. The computing device may determine whether the wireless analyzer should be provided with network access 210 based on, for example, certain credentials (e.g., user/device identification, password, etc.) or may be set to automatically provide network access once secure communication has been established 208 between the computing device and wireless analyzer. Communication 208 between the computing device and wireless analyzer may continue until (i) a requested access credential has been communicated to the wireless analyzer 210, (ii) the session has terminated 224, or (iii) a session time-out flag 218 has been indicated.

A primary objective of the wireless connection is to provide a secure, encrypted, virtual, digital tunnel between the computing device and the wireless analyzer, allowing for safe transmission of primary network access credentials. The wireless analyzer may communicate these primary wireless network access credentials to the primary wireless network 214 using, for example, an IEEE-802.11 connection. The primary wireless network access credentials are used to establish a secure communication connection 226 (e.g., a secure IEEE-802.11 connection) between the wireless analyzer and the primary network (e.g., wireless hospital network) and to exchange secure communications and/or transfers 216 using said secure connection until the session has (i) terminated 222 or (ii) a session time-out flag 220 has been indicated. For example, the wireless analyzer may use the secure communication connection (e.g., TLS, SSL, or other encryption methods using, for example, primary network access credentials) to communicate blood analysis patient data with said primary wireless network. Blood analysis patient data may include, for example, patient blood test results such as analyte concentrations, time and date of test, patient identification and user identification. The entire initiation and connection process may be done automatically without the need for the wireless analyzer user to perform any substantive operations, optionally initiating the entire process with a simple "activate" instruction.

Once a wireless analyzer has obtained the necessary access credentials to establish secure communication with a primary network, the wireless analyzer may repeatedly access said primarily wireless network without requiring further communication via the wireless network unless the access credentials are no longer valid or unavailable. For example, if a primary wireless network requires certain access credentials (e.g., "Certificate A"), once the wireless analyzer has obtained Certificate A, the wireless analyzer may freely access the primary wireless network without needing to communicate with a computing device via the wireless network. However, if, for whatever reason, the primary wireless network's security settings are adjusted to require different access credentials (e.g., "Certificate B"), the wireless analyzer may need to communicate with a computing device via the wireless network to obtain Certificate B. The need to communicate with the computing device via the wireless network may also arise, for example, in instances where the wireless analyzer's memory has been erased (voluntarily or involuntarily), become corrupt, or the wireless analyzer is attempting to connect to a different primary wireless network.

FIG. 3 is a flow diagram illustrating a process of connecting to a primary network. Upon initiation 302 (e.g., activating the device or the triggering of a "connect" button), a wireless analyzer having received the necessary access credentials may search for available primary wireless network access points 304. If no access points are found 306, or if none of the access points are in the configured access point list (the list being based on the available access credentials), then the wireless analyzer may enter sleep/power-save mode 308 for a preset period of time (e.g., 10 seconds). After the preset period of time has elapsed 314, the wireless analyzer may repeat the access point scan 304. Using a counter 314, this cycle may repeat for a preset number of attempts 310 (e.g., 3 attempts) after which the wireless analyzer may switch to command state 312. If the attempt limit has not been met, the access point scan may be repeated.

If a configured access point is found, the wireless analyzer may attempt to connect to the access point 318 using the parameters supplied in the access point configuration. If more than one configured access point is found 316, the wireless analyzer may attempt to communicate with the access point having the strongest signal first 320 (e.g., the access point having the strongest received signal strength indicator (RSSI)). The wireless analyzer may be further enabled to read the signal strength (e.g., RSSI) of the connection between the access point and the wireless module (e.g., an Ezurio wireless module) using either an internal or external antenna. The signal strength may be further displayed on the screen of the wireless analyzer to provide the user with an indication of the signal strength (e.g., a series of bars). If this communication attempt fails, communication with the second strongest configured access point may be attempted. If this communication attempt also fails, communication with the third strongest configured access point may be attempted and so on until all configured access points have been exhausted or a connection has been established. If all access points have been exhausted, the wireless analyzer may return to the sleep/power-save mode cycle 308 described above. Once the wireless analyzer has connected 322 with an access point, the wireless analyzer may exchange data and/or secure communications with the primary network (e.g., wireless hospital network) 324 until the session has either terminated 326 or a time-out flag 328 has been indicated. This initiation and connection process may be done automatically without the need for the wireless analyzer user to perform any substantive operations, optionally initiating the entire process with a simple "activate" or "connect" instruction. Furthermore, once communication between the wireless analyzer and primary wireless network is established 324, the wireless analyzer may allow roaming between access points in the event of either low signal-to-noise (SNR) or low received signal strength indicator (RSSI) conditions being detected 330.

In addition to using the secure connection to communicate health-care data, the secure connection and/or process may be used to update firmware, software and/or patches on the wireless analyzer. A configuration server, which would be in communication with, or incorporated into, the primary wireless network, may be a PC application capable of communicating new configuration files, patches, and/or software or software updates to remote modules (e.g., wireless analyzers). For example, the configuration server may be implemented as a Java application, which may be run under Linux, Windows, or another operating system. Each file of transactional keys may be allocated a version number (e.g., a 16-bit CRC of the contents of the configuration file) which may be stored in the module when the transactional key file is transferred and adopted by the module.

For example, when a remote module connects to the primary wireless server, the module version number may be compared to the latest version number available for download. If the version number in the module is different from the latest version available, the more recent configuration file is downloaded and/or installed to the module. The wireless analyzer may also be enabled to update (e.g., download and install) firmware, software and/or patches from another wireless analyzer using wireless communication (e.g., Wi-Fi, RFID, Bluetooth®, etc.).

In addition to software upgrades, the wireless analyzer may also communicate data via said primary wireless network, e.g., help files, instrument calibration coefficients, user customizations, patient customizations, language packs, instrument self-validation protocols, value assignment sheets for control fluids, instrument self-testing protocols, usage statistics, non-usage statistics, analyzer errors, CLEW (coefficients, limits & extrapolation windows), operator qualifications, and operator monitoring. In certain embodiments, the primary wireless network may poll a wireless analyzer within range to check parameters such as battery level and/or battery state of charge, presence in the Wi-Fi zone, or dynamic location of a wireless analyzer (e.g., location tracking).

The wireless analyzer may further include a disable/lock mechanism to ensure unauthorized personal do not tamper with the wireless analyzer. The disable/lock mechanism may be enabled/disabled via the secure network, via the wireless analyzer's input device (e.g., keyboard, keypad, touch screen, etc.) or automatically if the wireless analyzer has been idle for a preset period of time. The wireless analyzer may be enabled to automatically lock/disable if the wireless analyzer is out of range, meaning, for example, the wireless analyzer is unable to locate any primary wireless network access points. In this situation, the wireless analyzer may remain locked until the device is unlocked by the user or via the primary wireless network. In any of these situations, to unlock the wireless analyzer, the wireless analyzer, or computer in communication with the primary wireless network, may require, for example, the user to enter a username, password, and/or biometric identification.

Figure 4A:
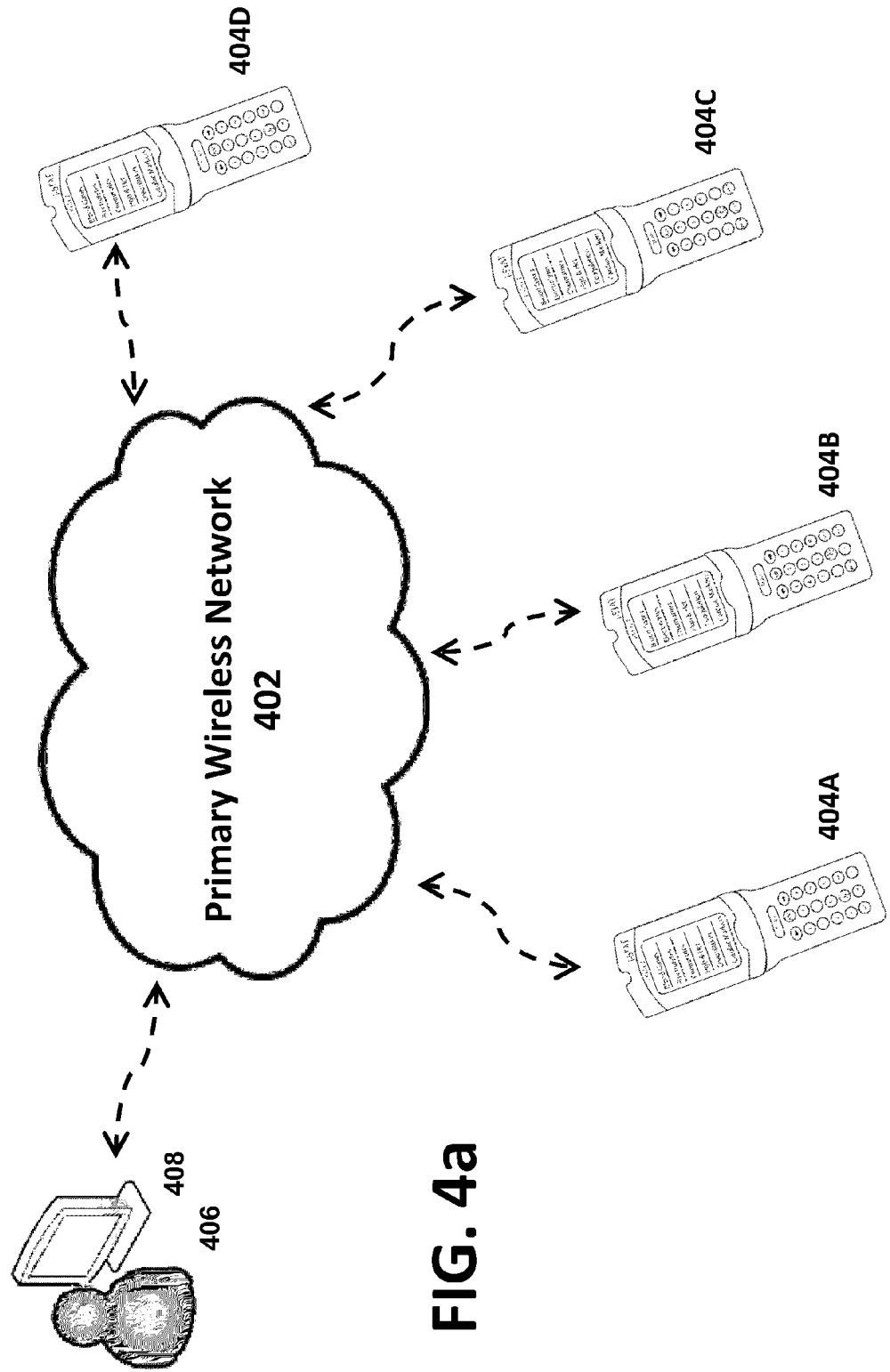
FIG. 4a is a diagram showing multiple wireless analyzers in communication with a point of care coordinator (POCC)
Figure 4B:
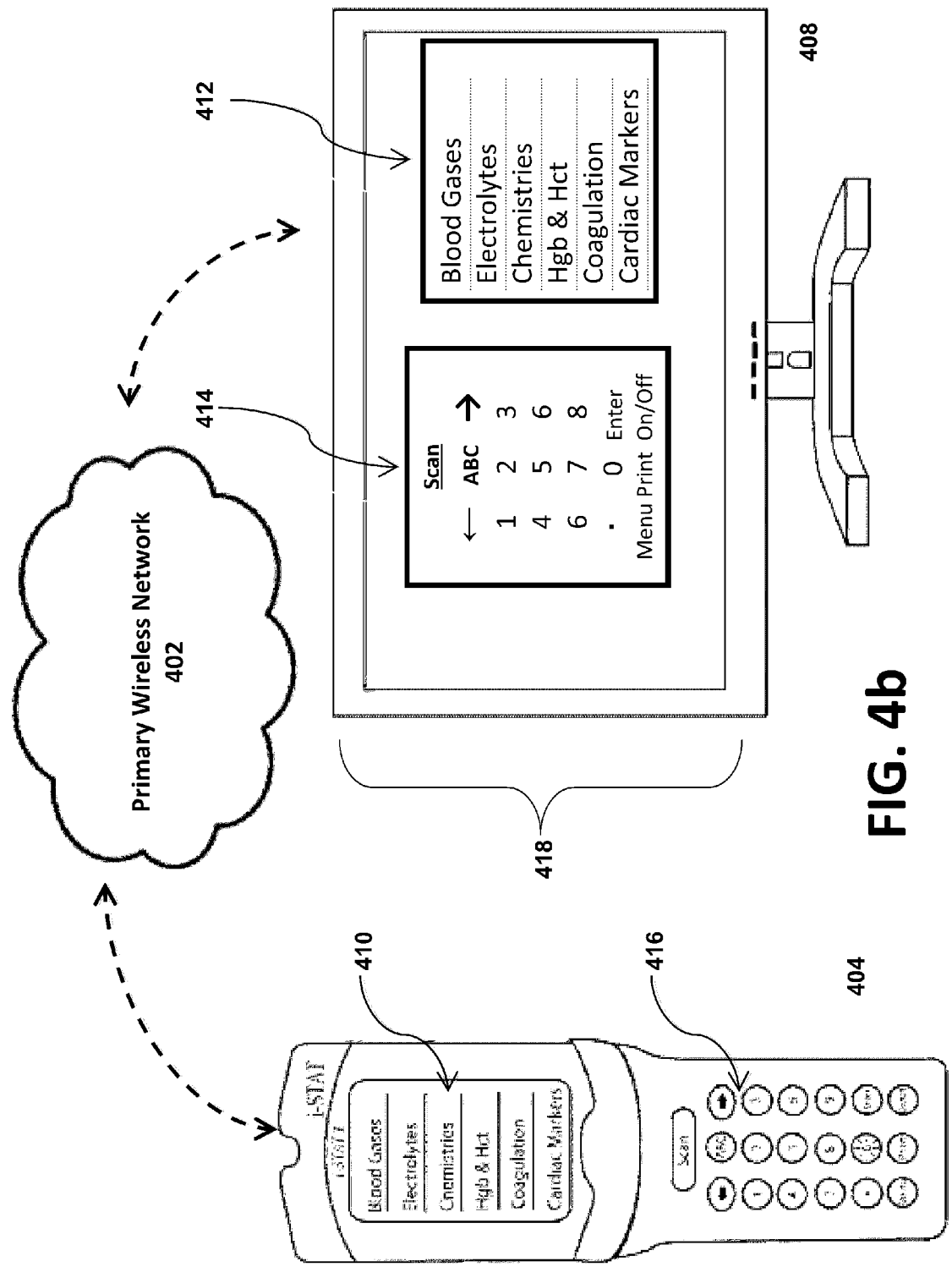
FIG. 4b is a diagram showing the simultaneous display of a wireless analyzer screen shot on both the wireless analyzer and a computer.

In some embodiments, as depicted in FIGS. 4a and 4b, it may be favorable to provide a view of the wireless analyzer 404 screen 410 on a computer 408 via a secure connection to the primary wireless network 402. For example, a point of care coordinator (POCC) 406 or technical support person may wish to view a screen shot 412 of the wireless analyzer's 404 screen 410 (or similar summary of information from analyzer 404), e.g., as either a still-shot or dynamically on computer 408 connected to the primary wireless network 402. This configuration would be useful for both remote patient monitoring by a third parties and/or providing technical assistance in the event of malfunction. To provide further functionality and control, the POCC 406 and/or technical support person may be further able to control a desired wireless analyzer 404 using the computer 408 connected to the primary wireless network 402. In this situation, a wireless analyzer control device 414 may be provided to the POCC 406 and/or technical support person enabling him or her to remotely control the desired wireless analyzer 404. This may be accomplished, for example, by providing a virtual wireless analyzer controller display 414 on the computer screen 418 to mimic the buttons/inputs 416 on the physical wireless analyzer 404.

Additionally, the POCC 406 may be alerted via computer 408, for example: when a user incorrectly uses a wireless analyzer 404; when battery level has dropped to a predetermined level; when wireless analyzer 404 deviates from normal results; when an wireless analyzer 404 is dropped or physically damaged (e.g., using shock/trauma sensing circuits); and/or when a wireless analyzer 404 self-check fails or fails to boot/initiate/activate. Similarly, the wireless analyzer may automatically wake up and contact the data manager within programmable intervals from, for example, 10 minutes to 24 hours.

Referring now to FIG. 4c, wireless analyzers 404A, 404B, 404C, 404D in communication with the primary wireless network 402 may be enabled act as a hub, or "hot spot" or router, for a another wireless analyzer 404E (e.g., a near-by wireless analyzer that is unable to locate and/or detect an access point signal). When a wireless analyzer 404A is acting as a router, the wireless analyzer 404A in communication with the primary wireless network 402 may wirelessly communicate (e.g., Wi-Fi, RFID, Bluetooth®, etc.) with another wireless analyzer 404E and relay any information between the wireless analyzer 404E and the primary wireless network 402. Essentially, wireless analyzer 404E communicates with the primary wireless network 402 using wireless analyzer 404A as a node.

The computer 408 connected to the primary wireless network may even allow custom messages (e.g., specialized training and/or other information) to be displayed on an analyzer information screen 410. This information could be emergency information or specific training information for only a particular subset of the analyzer population. For example, if a certain subset of patients may be impacted by a hospital malfunction or event, messages may be sent to those patients' wireless analyzers 404, via the primary wireless network 402, notifying health-care providers of the appropriate steps to take (e.g., evacuation, relocation, etc.). A custom message may be sent to a wireless analyzer 404 based on the physical location of the wireless analyzer 104 using device tracking techniques (discussed in greater detail below). A network 402 linking the wireless analyzers 404 would also permit standardization of information. For example, each wireless analyzer 404 may synchronize the time with the primary network 402 server computer clock or atomic clock. Standardization of the clocks would eliminate inaccurate time entries when reporting results, eliminate backdating the analyzer, and ensure an accurate time should a wireless analyzer momentarily lose power (e.g., due to battery failure or depletion).

In another embodiment, the computer 408 connected to the primary wireless network 402 may be enabled to track and report the status and location of a wireless analyzer 404 and/or other device on the primary wireless network. The portable nature of the wireless analyzer makes it easy to misplace, lose and/or steal. Furthermore, the capital cost associated with a wireless analyzer may be high. Thus, a system, as disclosed herein, for locating and tracking said wireless analyzer 404 may reduce costs associated with replacement due to misplacement, loss, or theft.

The portable wireless analyzer 404 may be tracked in a number of ways. For example, in some embodiments, the wireless analyzer 404 may be enabled to include and perform GPS and/or other triangulation techniques. Triangulation is a process by which the location of a portable device can be determined by measuring either the radial distance or the direction of the received signal from two or more different points. GPS, an advanced form of triangulation, currently uses 24 orbiting satellites to pinpoint the geographic location or a device. Currently, the location accuracy range is anywhere from 100 to 10 meters for most equipment. However, accuracy can be pinpointed to within one meter with special military-approved equipment.

In lieu of triangulation, location can be calculated based on the principle of the time difference between the receipt of signals from a pair of radio transmitters (access points). A given constant time difference between the signals from the two stations can be represented by a hyperbolic line of position (LOP). If the positions of the two synchronized access points are known, the position of the wireless analyzer can be determined as being somewhere on a particular hyperbolic curve where the time difference between the received signals is constant. Under ideal conditions, this is proportionally equivalent to the difference of the distances between the receiver and each of the two stations. A similar system was used by LORAN (Long Range Navigation), a terrestrial radio navigation system using low frequency radio transmitters in multiple deployments (multilateration) to determine the location and speed of the receiver.

More specifically, RFID may be used to track and locate a wireless analyzer. RFID is generally divided into Active and Passive technologies. Active RFID devices are typically battery powered devices typically employing some silicon logic to provide autonomous date transmission and may even incorporate programmable data storage to hold, for example, pricing, routing or other data in the device. Passive technologies are often divided into fully passive and battery assisted passive devices. These passive devices are generally used in poll/response systems and require a stimulus to provide a response. Inventory monitoring, retail items and medical supplies alike are generally tracked by passive RFID means. The direction taken by the real time location services (RTLS) market has been to universally use active RFID for tags and devices. There are two general approaches to RTLS: 1) Proprietary tags that interact with tracking hardware/software or middleware that interfaces with enterprise software; and 2) Fully associated IEEE-802.11 devices (tags, PDAs, laptop computer, etc.) that communicate with location appliance hardware/software or middleware to interface with enterprise software.

Proprietary tags may be divided into custom infrastructure and general infrastructure based on IEEE-802.11 wireless. Systems based on tag communication at 433 MHz, 900 MHz, infrared, and sonic solutions are typically closed systems using a common vendor for supplying tags, tag receivers, possibly concentrators, and middleware. This type of system is exemplified by vendors such as: Radiance, Awarepoint, Radarfind, and Versas. For example, Versas uses a tag that communicates via IEEE-802.11 but only uses the data entry point from the network. Further refinement of the location may be accomplished by transmitting payload data identifying received data from IR emitters liberally located in the area of interest. In the cases mentioned above, an enterprise WLAN may be utilized as the final link from the enterprise software or vendors middleware to the enterprise software.

A IEEE-802.11x system involves at least one radio device installed within the analyzer. Two possible RTLS structures and protocols for active location service include ISO-246730 based service and generic IEEE-802.11 b/g service. However, both services may be based on IEEE-802.11b/g and both may have some measure of support in the location field. Fully Associated IEEE-802.11 tags resemble a normal IEEE-802.11 connection and may also track portable devices. For example, WhereNet has announced a tag that may work as either IEEE-802.11(b) or ISO-24730. G2 Microsystems, manufacturer of the chip used by WhereNet, offers a low-power system-on-a-chip and related module that enables Wi-Fi to be used in a wider range of applications that use smaller batteries, like remote controls and asset tracking tags. For example, G2 Microsystems produces the G2C547 chip, a combination IEEE-802.11 and ISO-24730 radio chip that may be integrated with a portable device to enable device tracking.

The ISO-24730 location implementation typically centers on a hardware subsystem that communicates with cooperative access points to gather data about the message arrival time of "beacon" transmissions from the tag or signal strength reported by the tag. The beacon may be a multicast message where the transmitter may not be required to be associated with any access point. In operation, the access point records the time of arrival of the message and the payload reports the signal strength. These values may be forwarded to the location services hardware and an attempt may be made to triangulate the tag/emitter relative to the access points. Accuracy is routinely measured within 3 meters. Furthermore, the position of the wireless analyzer may be displayed by vendor or enterprise software and, in the case of higher functionality software, may be overlaid on a map of the facility.

The access point may be part of an Extended Service Set (ESS) such that the broadcast Service Set Identifier (SSID) would not be unique to a particular access point. Access points that are a collection of Basic Service Set (BSS) devices could each have a unique SSID.

Examining the transactions that occur within a normal IEEE-802.11 connection reveals that the wireless analyzer's integrated mobile radio, when fully associated with an access point, knows the Access point ID (i.e., the MAC address) of the access point. This information, if contained in the payload of transmission from an analyzer, could uniquely identify the access point used in the transaction. Thus, data manager software receiving results from an analyzer via wireless link may be able to identify the MAC address of an access point. To provide the location of the portable device, the data manager software may also provide a means of associating MAC address to physical locations in, for example, a hospital.

Therefore, it is possible to provide a "Find Me" location service by providing or using an existing IEEE-802.11 radio in the wireless analyzer hardware. To support this location service, the radio device should be chosen to provide a low level access Application Programming Interface (API) to permit the Access Point ID (MAC Address) to be known and included in the payload transmitted by the analyzer. This mode typically requires that the analyzer be fully associated with an access point in a normal 802.11 mode while also providing the capability to implement a ISO-24730 RTLS protocol without additional hardware cost.

The various device tracking technologies may be useful in monitoring/tracking patients and/or equipment within communication range of the primary wireless network. Furthermore, the ability to track and monitor the wireless analyzers would play a role in managing wireless analyzers inventory. For example, if the computer on the wireless network indicates that an abundance of wireless analyzers were located in the ICU but there was a shortage in the ER, wireless analyzers could be relocated to meet the needs of the institution.

In some embodiments, the wireless analyzer may include a paging device capable of alerting people in proximity to the wireless analyzer. For example, a "start alarm" signal may be sent to a wireless analyzer via a secured connection, causing the wireless analyzer to sound an alarm and/or other alerting means (e.g., vibration, lights, etc.). Once the wireless analyzer has been located, the user may silence the alarm by pressing a button (either physical or via touch screen) on the wireless analyzer and/or an "end alarm" signal may be communicated to the wireless analyzer via the secured connection.

In some embodiments, the present invention may also be directed to a system and method for connecting other wireless-enabled portable devices to a primary wireless network. For example, a computer with embedded preselected access credentials may be connected to a wireless network to establish a connection between the computer and a portable device acting as a WAP via a secure connection. The computer may then communicate/transfer the access credentials to the portable device over the wireless network. After closing the wireless connection, the portable device may then authenticate connection to a primary wireless network by communication of the access credentials with the primary wireless network. This process may be automatically repeated for portable devices at various locations.

Although various embodiments have been described with reference to a particular arrangement of parts, features, and the like, these are not intended to exhaust all possible arrangements or features, and indeed many other embodiments, modifications, and variations will be ascertainable to those of skill in the art.

All U.S. and foreign patent documents, and all articles, brochures, and all other published documents discussed above are hereby incorporated by reference into the Detailed Description.

What is claimed is:

1. A system for establishing a wireless network in point of care testing, the system comprising:
 a wireless analyzer configured to authorize wireless access to said wireless analyzer, and read a patient health parameter;
 a computing device configured to obtain said wireless access with said wireless analyzer using a wireless network identifier, and communicate access credentials to said wireless analyzer via said wireless access; and
 a primary wireless network configured to communicate with said wireless analyzer, authenticate a secure connection with said wireless analyzer using said access credentials, and receive said patient health parameter via said secure connection,
 wherein the wireless analyzer comprises a wireless access point (WAP) module configured to authorize the computing device to obtain the wireless access to the wireless analyzer.

2. The system of claim 1, wherein:
said wireless analyzer is configured to act as a dynamic host configuration protocol (DHCP) server; and
said computing device is further configured to receive input from said wireless analyzer comprising network IP parameters to obtain said wireless access with said wireless analyzer.

3. The system of claim 1, wherein:
said wireless analyzer is further configured such that said wireless analyzer does not broadcast said wireless network identifier; and
said computing device is further configured to receive input comprising the wireless network identifier.

4. The system of claim 1, wherein:
said wireless analyzer is further configured to broadcast said wireless network identifier; and
said computing device is further configured to search for said broadcasted wireless network identifier.

5. The system of claim 4, wherein:
said wireless analyzer comprises an antenna; and
the WAP module is further configured to broadcast said wireless network identifier.

6. The system of claim 5, wherein:
said wireless analyzer further comprises a host processor, random access memory (RAM), and read only memory (ROM); and
said host processor is configured to control said WAP module.

7. The system of claim 6, wherein:
said host processor is further configured to activate said WAP module based on user settings or instructions; and
said broadcasted wireless network identifier is a service set identifier (SSID) that identifies said wireless analyzer.

8. The system of claim 7, wherein said user settings or instructions include at least one of the following settings or instructions:
said wireless analyzer authorizing said wireless access from any computing device;
said wireless analyzer authorizing said wireless access from one or more specified computing devices according to a specified password; and
said wireless analyzer automatically authorizing said wireless access from one or more specified computing devices.

9. The system of claim 1, wherein:
said wireless network identifier is a service set identifier (SSID) that identifies said wireless analyzer; and
said SSID is a known SSID or said SSID is comprised from a unique name.

10. The system of claim 9, wherein said unique name comprises: (i) a MAC address of said wireless analyzer, (ii) a serial number of said wireless analyzer, or (iii) a combination thereof.

11. The system of claim 1, wherein:
said wireless network identifier is a service set identifier (SSID) that identifies said wireless analyzer; and
said SSID is dynamically generated.

12. The system of claim 1, wherein said wireless access comprises a secure network between said wireless analyzer and said computing device, said secure network comprising: a secure socket layer (SSL) connection, a transport layer security (TLS) connection, an SSL/TLS connection, a pre-shared key (PSK) connection, a WiFi Protected Access (WPA) connection, a WPA1 connection, a WPA2 connection, a WPA-Enterprise (WPA-802.1x) connection, any other cryptographic or encryption protocol connection, or any combination thereof.

13. The system of claim 12, wherein said wireless analyzer comprises a unique certificate or requests said unique certificate from said computing device, wherein said unique certificate is used in establishing said secure network.

14. The system of claim 1, wherein said computing device communicates said access credentials with said wireless analyzer via said wireless access using simple network management protocol (SNMP).

15. The system of claim 1, wherein said wireless analyzer may repeatedly access said primary wireless network without requiring further communication with said computing device.

16. The system of claim 1, wherein said secure connection comprises an SSL connection, a TLS connection, an SSL/TLS connection, or combinations thereof.

17. The system of claim 1, wherein:
said primary wireless network comprises a hospital wireless network; and
said hospital wireless network comprises a connection with a laboratory information system or hospital information system.

18. The system of claim 1, wherein said wireless analyzer is further configured to perform a function via said primary wireless network, the function comprising: (i) communicating location of said wireless analyzer; (ii) receiving and displaying a custom message; (iii) communicating and installing software updates; (iv) communicating print requests with a printer in communication with said primary wireless network; (v) communicating battery level of said wireless analyzer; (vi) communicating dynamic display information with another computing device in communication with said primary wireless network; (vii) synchronizing time with said another computing device in communication with primary wireless network; (viii) providing network access to another wireless analyzer; or (ix) combinations thereof.

19. The system of claim 1, wherein said wireless analyzer is further configured to communicate patient test results with said primary wireless network, the patient test results comprising: (i) said patient health parameter, (ii) time of test, (iii) date of test, (iv) patient identification, (v) user identification, or (vi) combinations thereof.

20. The system of claim 1, wherein said wireless analyzer is further configured to communicate information with said primary wireless network, the information comprising: (i) an instrument calibration coefficient; (ii) an instrument self-validation test result; (iii) an instrument self-testing result; or (iv) combinations thereof.

21. The system of claim 1, wherein said wireless analyzer is further configured to receive data communicated from said primary wireless network, the data comprising: (i) software upgrade; (ii) an instrument calibration coefficient; (iii) an instrument self-validation protocol; (iv) an instrument self-testing protocol; or (v) a combinations thereof.

22. A method of connecting a wireless analyzer to a primary wireless network, the method comprising the steps of:
receiving at said wireless analyzer a request for wireless access to said wireless analyzer from at least one computing device, wherein said wireless analyzer is configured to read a patient health parameter, and said at least one computing device is configured to receive a wireless network identifier identifying said wireless analyzer as a wireless access point (WAP) to send said request for said wireless access;
authorizing said wireless access to said wireless analyzer;
receiving at said wireless analyzer access credentials for said primary wireless network from said at least one computing device;

terminating said wireless access with said at least one computing device; and
authenticating a secure connection between said wireless analyzer and said primary wireless network using said access credentials.

23. The method of claim 22, wherein a server assigns said wireless network identifier to said at least one computing device.

24. The method of claim 22, wherein said wireless analyzer performs a routing function for said at least one computing device once said wireless access is authorized.

25. The method of claim 22, further comprising:
broadcasting said wireless network identifier using said wireless analyzer; and
sending said patient health parameter from said wireless analyzer to said primary wireless network using said secure connection.

26. The method of claim 25, wherein said wireless analyzer may repeatedly access said primary access network without requiring further communication with said at least one computing device.

27. The method of claim 26, wherein:
said secure connection comprises an secure socket layer (SSL) connection, a transport layer security (TLS) connection, an SSL/TLS connection, or combinations thereof; and
said wireless network identifier is a service set identifier (SSID) that identifies said wireless analyzer.

28. The method of claim 27, wherein:
said primary wireless network comprises a hospital wireless network; and
said hospital wireless network comprises a connection with a laboratory information system or hospital information system.

29. A wireless analyzer enabled for secure communication with a primary wireless network, the wireless analyzer comprising:
a display;
an input device;
a sensing apparatus for detecting a patient health parameter;
an antenna;
a wireless access point (WAP) module configured to establish a wireless connection with said wireless analyzer from a computing device using a wireless network identifier, and obtain at least one access credential for said primary wireless network from said computing device; and
a host processor configured to authenticate a secure wireless connection with said primary wireless network using said at least one access credential.

30. The wireless analyzer of claim 29, wherein:
the WAP module is further configured to broadcast said wireless network identifier; and
the host processor is further configured to send said patient health parameter from said wireless analyzer to said primary wireless network using said secure wireless connection.

31. The wireless analyzer of claim 29, wherein:
said host processor is further configured to activate said WAP module based on user settings or instructions; and
said wireless network identifier is a service set identifier (SSID) that identifies said wireless analyzer.

32. The wireless analyzer of claim 31, wherein said user settings include at least one of the following settings or instructions:
said wireless analyzer authorizing said wireless connection from any computing device;
said wireless analyzer authorizing said wireless connection from one or more specified computing devices according to a specified password; and
said wireless analyzer automatically authorizing said wireless connection from one or more specified computing devices.

33. The wireless analyzer of claim 29, wherein:
said wireless network identifier is a service set identifier (SSID) that identifies said wireless analyzer; and
said SSID is a known SSID or said SSID is comprised from a unique name.

34. The wireless analyzer of claim 33, wherein said unique name comprises: (i) a MAC address of said wireless analyzer, (ii) a serial number of said wireless analyzer, or (iii) combinations thereof.

35. The wireless analyzer of claim 34, wherein said wireless connection comprises a secure network between said wireless analyzer and said computing device, said secure network comprising: a secure socket layer (SSL) connection, a transport layer security (TLS) connection, an SSL/TLS connection, a pre-shared key (PSK) connection, a WiFi Protected Access (WPA) connection, a WPA1 connection, a WPA2 connection, a WPA-Enterprise (WPA-802.1x) connection, any other cryptographic or encryption protocol connection, or any combination thereof.

36. The wireless analyzer of claim 35, wherein said wireless analyzer further comprises a unique certificate or requests said unique certificate from said computing device, wherein said unique certificate is used in establishing said secure network.

37. The wireless analyzer of claim 36, wherein said computing device communicates said access credentials with said wireless analyzer via said wireless connection using simple network management protocol (SNMP).

38. A computer program product comprising a non-transitory computer usable storage medium having readable program code embodied in the storage medium, the computer program product includes at least one component operable to:
receive at a wireless analyzer a request for wireless access to said wireless analyzer from at least one computing device, wherein said wireless analyzer is configured to read a patient health parameter, and said at least one computing device is configured to use a wireless network identifier identifying said wireless analyzer as a wireless access point (WAP) to send said request for said wireless access;
authorize said wireless access to said wireless analyzer;
receive at said wireless analyzer access credentials for a primary wireless network from said at least one computing device;
terminate said wireless access with said at least one computing device; and
authenticate a secure connection between said wireless analyzer and said primary wireless network using said access credentials.

39. The computer program product of claim 38, wherein the at least one component is further operable to:
broadcast said wireless network identifier using said wireless analyzer; and
send said patient health parameter from said wireless analyzer to said primary wireless network using said secure connection.

* * * * *